United States Patent
Philippon et al.

(10) Patent No.: US 9,302,266 B2
(45) Date of Patent: Apr. 5, 2016

(54) CLAMP SUITABLE FOR GRIPPING A BIOLOGICAL SAMPLE HOLDER, ASSEMBLY CONSISTING OF A BIOLOGICAL SAMPLE HOLDER AND A SUITABLE CLAMP, AND TREATMENT AND/OR ANALYSIS MACHINE

(71) Applicant: Noviloire SA, Roanne (FR)

(72) Inventors: Michel Philippon, Perreux (FR); Sebastien Bernay, Ecoche (FR)

(73) Assignee: BIO RAD INNOVATIONS, Marnes la Coquette (FR)

( * ) Notice: Subject to any disclaimer, the term of this patent is extended or adjusted under 35 U.S.C. 154(b) by 0 days.

(21) Appl. No.: 14/543,500

(22) Filed: Nov. 17, 2014

(65) Prior Publication Data

US 2015/0071820 A1    Mar. 12, 2015

Related U.S. Application Data

(62) Division of application No. 12/996,580, filed as application No. PCT/FR2009/051068 on Jun. 5, 2009, now Pat. No. 8,920,721.

(30) Foreign Application Priority Data

Jun. 6, 2008    (FR) ..................................... 08 53786

(51) Int. Cl.
*B01L 9/00*    (2006.01)
*G01N 35/00*    (2006.01)
*G01N 35/02*    (2006.01)
(Continued)

(52) U.S. Cl.
CPC . *B01L 9/50* (2013.01); *B01L 9/523* (2013.01); *G01N 35/0099* (2013.01); *G01N 35/028* (2013.01); *G01N 35/04* (2013.01); *B01L 2200/141* (2013.01); *B25J 15/0033* (2013.01);
(Continued)

(58) Field of Classification Search
CPC .............. G01N 35/0099; B25J 15/0033; B25J 15/0042
See application file for complete search history.

(56) References Cited

U.S. PATENT DOCUMENTS

| 4,336,926 | A | 6/1982 | Inagaki et al. |
| 5,681,530 | A | 10/1997 | Kuster et al. |

(Continued)

FOREIGN PATENT DOCUMENTS

| EP | 0 895 087 A2 | 2/1999 |
| ES | 2 156 670 | 5/2002 |
| JP | 9-201788 | 8/1997 |
| WO | WO 02/068157 A2 | 9/2002 |
| WO | WO 2005/102617 A1 | 11/2005 |

*Primary Examiner* — P. Kathryn Wright
(74) *Attorney, Agent, or Firm* — Davidson, Davidson & Kappel, LLC

(57) ABSTRACT

A machine for treatment and/or analysis of biological samples, including a hinged arm to which a clamp for gripping a first biological sample holder is fixed. The clamp including first and second arms able to move relative to each other along a gripping position between a first position of gripping the first biological sample holder, and a first position of releasing the biological sample holder. Each arm of the clamp includes a groove. When the first and second arms are in the first position of release, the first and second grooves are spaced away from each other along the gripping direction, and when the first and second arms are in the first gripping position, the first and second grooves are brought closer to each other along the gripping direction, so as to be able to receive lateral edges of the first biological sample holder, so as to grip it by squeezing the lateral edges along the gripping direction.

11 Claims, 11 Drawing Sheets

(51) Int. Cl.
*G01N 35/04* (2006.01)
*B25J 15/00* (2006.01)

(52) U.S. Cl.
CPC ........... *B25J 15/0042* (2013.01); *G01N 35/026* (2013.01); *G01N 2035/042* (2013.01); *Y10S 901/31* (2013.01); *Y10S 901/36* (2013.01)

(56) References Cited

U.S. PATENT DOCUMENTS

| | | |
|---|---|---|
| 2002/0117380 A1 | 8/2002 | Downs et al. |
| 2004/0086368 A1 | 5/2004 | Downs et al. |
| 2007/0258858 A1 | 11/2007 | Rasnow et al. |

CLAMP SUITABLE FOR GRIPPING A BIOLOGICAL SAMPLE HOLDER, ASSEMBLY CONSISTING OF A BIOLOGICAL SAMPLE HOLDER AND A SUITABLE CLAMP, AND TREATMENT AND/OR ANALYSIS MACHINE

This is a Divisional of U.S. patent application Ser. No. 12/996,580, filed on Dec. 6, 2010, and hereby incorporated by reference herein.

The present invention concerns a clamp suitable for gripping a biological sample holder, an assembly consisting of a biological sample holder and a clamp suitable for gripping it, and a machine for treatment and/or analysis of biological samples.

BACKGROUND

The company GRIFOLS markets a biological sample treatment and analysis machine, comprising a clamp suitable for gripping a first biological sample holder comprising a wall provided with two opposite lateral edges, and biological sample receptacles carried by the wall, the wall extending along a direction intended, in normal use of the first biological sample holder, to be vertical with the receptacles opening upwardly, the clamp comprising first and second arms mobile in relation to each other along a gripping direction between a first position of gripping the first biological sample holder, and a first position of releasing the biological sample holder.

More precisely, this known clamp was designed to grip a "gel" type card that also comprises an upper rim, fixed to the upper edge of the main plate and perpendicular thereto. The upper rim extends over the entire length of the upper edge. The first and second arms extend downward from a base of the clamp. The first and second arms are intended to grip the gel card in the width of the upper rim, by the underside of the upper rim. The gripping is done in the middle of the length of the upper edge, with the base of the clamp facing said upper edge. To ensure the stability of the gel card, fingers also emerge from the base, downward, to surround the upper rim of the gel card.

Yet the biological sample receptacles of a gel card may emerge through the upper rim.

Thus, one drawback of the preceding known clamp is that there is a significant risk of contamination of the biological samples by the clamp.

SUMMARY OF THE INVENTION

An object of the invention is to propose a clamp suitable for gripping a gel card, with low risks of contamination of the biological samples.

To that end, the invention provides to a clamp of the aforementioned type, characterized in that: the first arm comprises a first groove; the second arm comprises a second groove; when the first and second arms are in the first releasing position, the first and second grooves are spaced apart from each other along the gripping direction; and when the first and second arms are in the first gripping position, the first and second grooves are brought closer to each other along the gripping direction and extend one facing the other, so as to be able to receive the lateral edges of the biological sample holder, in order to grip the biological sample holder by squeezing the lateral edges in the gripping direction.

Owing to the invention, it is not necessary for part of the clamp to be in contact with the upper rim of the gel card, which reduces the risk of soiling the biological samples.

According to another feature of the invention, the first groove has a first transverse profile whereof at least one portion is V-shaped along a first direction of the groove; the second groove has a second transverse profile whereof at least one portion is V-shaped along a second groove direction; and when the first and second arms are in the first gripping position, the V-shaped portion of the first profile and the V-shaped portion of the second transverse profile are open towards each other.

If the sample holder is stored in a basket not guaranteeing precise positioning, the presence of the V-shaped profiles still makes it possible to guide the wall towards the bottom of the groove, which favors good gripping by the clamp.

According to another feature of the invention, when the first and second arms are in the first gripping position, the first and second groove directions are parallel to each other to within 10° and perpendicular to the gripping direction to within 10°.

The lateral edges of a gel card being parallel to each other, this orientation of the grooves makes it possible to have a large contact length between each lateral edge and the groove receiving it, which allows stable squeezing of the gel card in the grooves.

According to another feature of the invention: the first arm comprises a first protruding portion, and the second arm comprises a second protruding portion; when the first and second arms are in the first gripping position, the first and second protruding portions protrude in relation to their respective arms along the gripping direction; and the first groove is formed in the first protruding portion, and the second groove is formed in the second protruding portion.

The protruding portions allow the arms to be spaced away from the gel card, which further reduces the risk of contamination via contact with or proximity to the upper rim, in particular in the case where the arms are connected to a base of the clamp intended to extend above the upper rim of the gel card.

According to another feature of the invention, the first groove comprises two open ends, and the second groove comprises two open ends.

According to another feature of the invention, on one hand, the clamp is suitable for gripping, in place of the first biological sample holder, a second biological sample holder comprising first and second opposite parallel lateral walls, an upper wall connecting the first and second lateral walls, and biological sample receptacles, carried by the upper wall, the first and second lateral walls being intended, in a normal use of the second biological sample holder, to extend vertically, with the receptacles opening upwardly, and, on the other hand: the first and second arms can move relative to each other along the gripping direction between a second position of gripping the second biological sample holder, and a second position of releasing the second biological sample holder, the first and second gripping positions being able to be identical, and the first and second releasing positions being able to be identical; the first arm comprises a first contact face with the first lateral wall of the second biological sample holder; the second arm comprises a second contact face with the second lateral wall of the second biological sample holder; when the first and second arms are in the second releasing position, the first and second contact faces are spaced apart from each other along the gripping direction; and when the first and second arms are in the second gripping position, the first and second contact faces are brought closer to each other along the gripping direction and are opposite each other, so as to be able to contact the first lateral wall and the second lateral wall of the second biological sample holder, respectively, in order to grip the biological sample holder by squeezing the first and second lateral walls along the gripping direction.

Owing to this feature, the same clamp is capable of gripping "microplates."

According to two other features of the invention:

the first arm comprises a first means for reducing sliding with the first lateral wall; and the second arm comprises a second means for reducing sliding with the second lateral wall; and the first means for reducing sliding comprises a first blade overhanging relative to the first contact face, the first overhanging blade being intended to be folded in contact with the first lateral wall; and the second means for reducing sliding comprises a second blade overhanging relative to the second contact face, the second overhanging blade being intended to be folded in contact with the second lateral wall.

Owing to one or the other of these feature, the clamp is capable of gripping sample holders having smooth lateral walls.

According to another feature of the invention: the first protruding portion comprises the first contact face, and the first contact face is separated in two by the first groove; and the second protruding portion comprises the second contact face, and the second contact face is separated in two by the second groove.

Thus, the bulk of the clamp is reduced.

According to other features of the invention:

the clamp comprises a means for detecting the presence of a gripped biological sample holder; and the clamp comprises a barcode reader to read a barcode inscribed on the biological sample holder.

The invention also provides an assembly of a first biological sample holder and a clamp according to the invention.

The invention also provides a biological sample treatment and/or analysis machine, characterized in that it comprises: a clamp according to the invention; a first station for treatment or analysis of biological samples received in the receptacles of a first biological sample holder; a first storage location for at least a first biological sample holder; and a hinged arm, to which the clamp is fixed, configured to move the clamp from the first storage location to grip a first biological sample holder, to the treatment or analysis station to release the first biological sample holder there, so that it can be treated or analyzed.

The term "treatment" designates any action on the biological samples, including pipetting into the receptacles of a biological sample holder.

According to one feature of the invention, on one hand, the machine comprises: a second station for treatment or analysis of biological samples received in the receptacles of a second biological sample holder; and a second storage location for at least a second biological sample holder, on the other hand, the hinged arm, to which the clamp is fixed, is configured to move the clamp from the second storage location to grip a second biological sample holder, to the treatment or analysis station to release the second biological sample holder there, so that it is treated or analyzed there.

BRIEF DESCRIPTION FO THE DRAWINGS

These features and advantages of the invention, as well as others, will appear upon reading the following description of one example of an embodiment of the invention. The description is done in reference to the appended drawings, in which.

DETAILED DESCRIPTION

The invention concerns the analysis of biological samples, whether they are transported in "gel" cards or "microplates."

In the context of the present invention, "biological sample holder" refers, in addition to all gel cards and all microplates, to any other form of biological sample container having the claimed structural features allowing it to be gripped by the clamp according to the invention.

Figure 1:
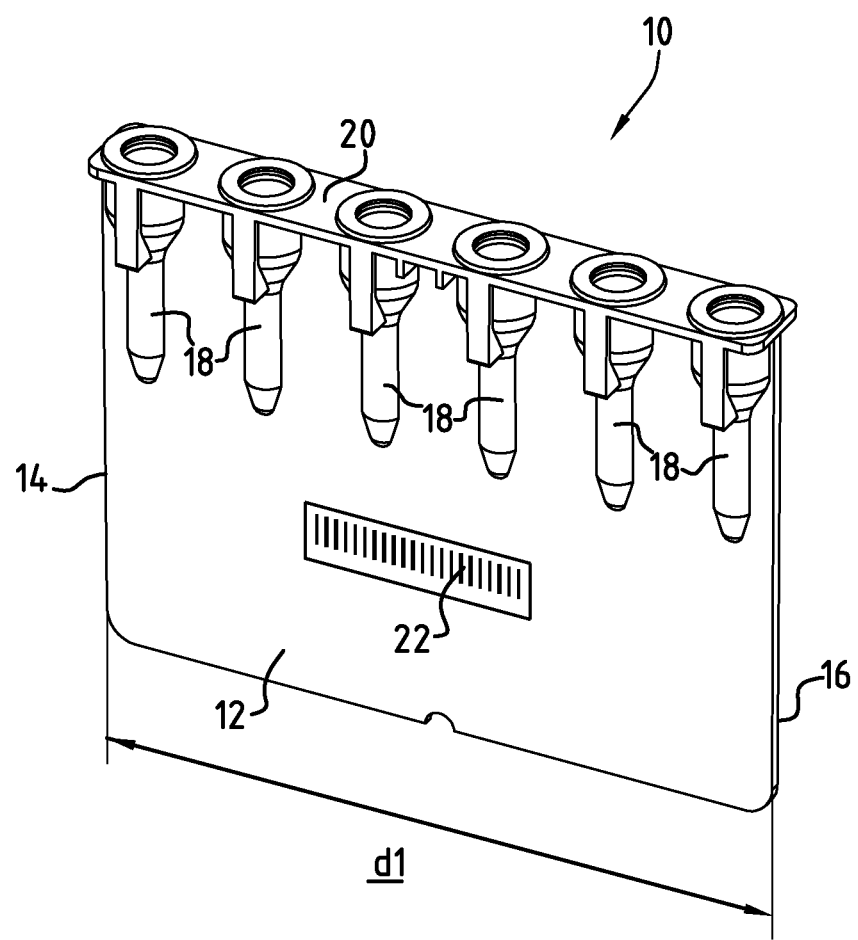
FIG. 1 is a perspective view of a "gel" card.

In reference to FIG. 1, a gel card 10, marketed for example by the company DIAMED, Cressier, Switzerland, forms a biological sample holder comprising a rectangular main wall 12, provided with two opposite lateral edges 14, 16. The gel card 10 also comprises an upper rim 20 fixed to the main wall 12 and extending between the two lateral edges 14, 16, perpendicular to the main wall 12. The gel card 10 also comprises biological sample receptacles 18, in the form of tubes 18, carried by the wall 12 and emerging through the upper rim 20. A gel card generally comprises six receiving tubes 18.

In normal use of the gel card 10, the main wall 12 and the tubes 18 extend along the vertical direction, with the upper rim 20 towards the top, so that the tubes 18 emerge upwardly, as shown in FIG. 1.

The gel card 10 also comprises a barcode 22 inscribed on one face 24 of the main wall 12, below the tubes 18.

The lateral edges 14, 16 generally have a height of 100 mm or less, for example 52 mm, and are separated by a length d1 of 140 mm or less, for example 70 mm. The main wall 12 has a thickness of 2 min or less, for example 1.2 mm, and a weight of 10 grams or less, for example 6 grams. The upper rim 20 has a width of 20 mm or less, for example 9 mm.

Figure 2:
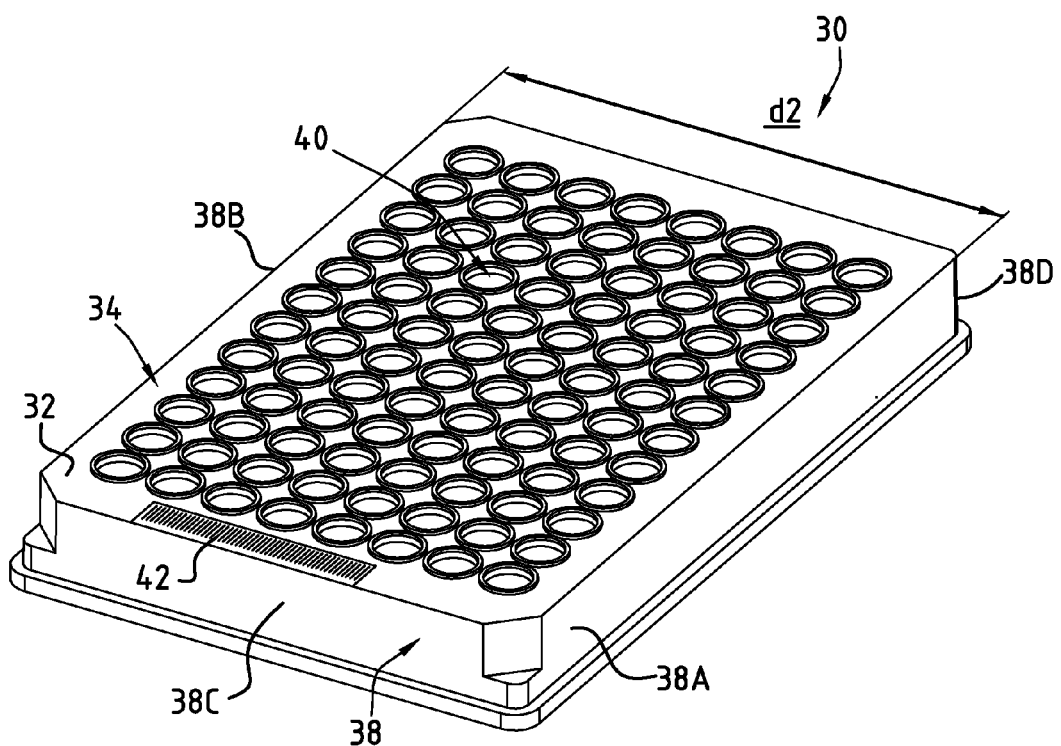
FIG. 2 is a perspective view of a "microplate"

In reference to FIG. 2, a microplate 30, which is for example marketed by NUNC, Denmark, forms a biological sample holder comprising a rectangular main wall 32 comprising an upper face 34. The microplate 30 also comprises lateral walls 38 extending perpendicular to the main wall 32 from the edges of that wall 32, opposite the upper face 34. The lateral walls 38 comprise first and second large lateral walls 38A, 38B, opposite and parallel to each other, and opposite transverse walls 38C, 38D.

The microplate 30 also comprises biological sample receptacles 40, in the form of half-cups, carried by the main wall 32. The receptacles 40 emerge through the upper face 34. The receptacles 40 are arranged in a matrix, for example 12 by 8 receptacles.

During normal use of the microplate 30, the main wall 32 is intended to be horizontal, with the upper face 34 upwards, so that the receptacles 40 emerge upwardly.

The microplate 30 also comprises a barcode 42 inscribed on the upper face 34 of the wall 32.

The microplate 30 is generally made from polystyrene and weighs less than 60 grams, generally 35 grams. Preferably, the wall 32 has dimensions smaller than 200 mm by 150 mm, for example 128 mm by 85 mm. The lateral walls 38 generally have a height of 30 mm or less, for example 15 mm. The first and second large lateral walls 38A, 38B are thus separated by a distance d2 smaller than 150 mm, for example 85 mm.

Figure 3:
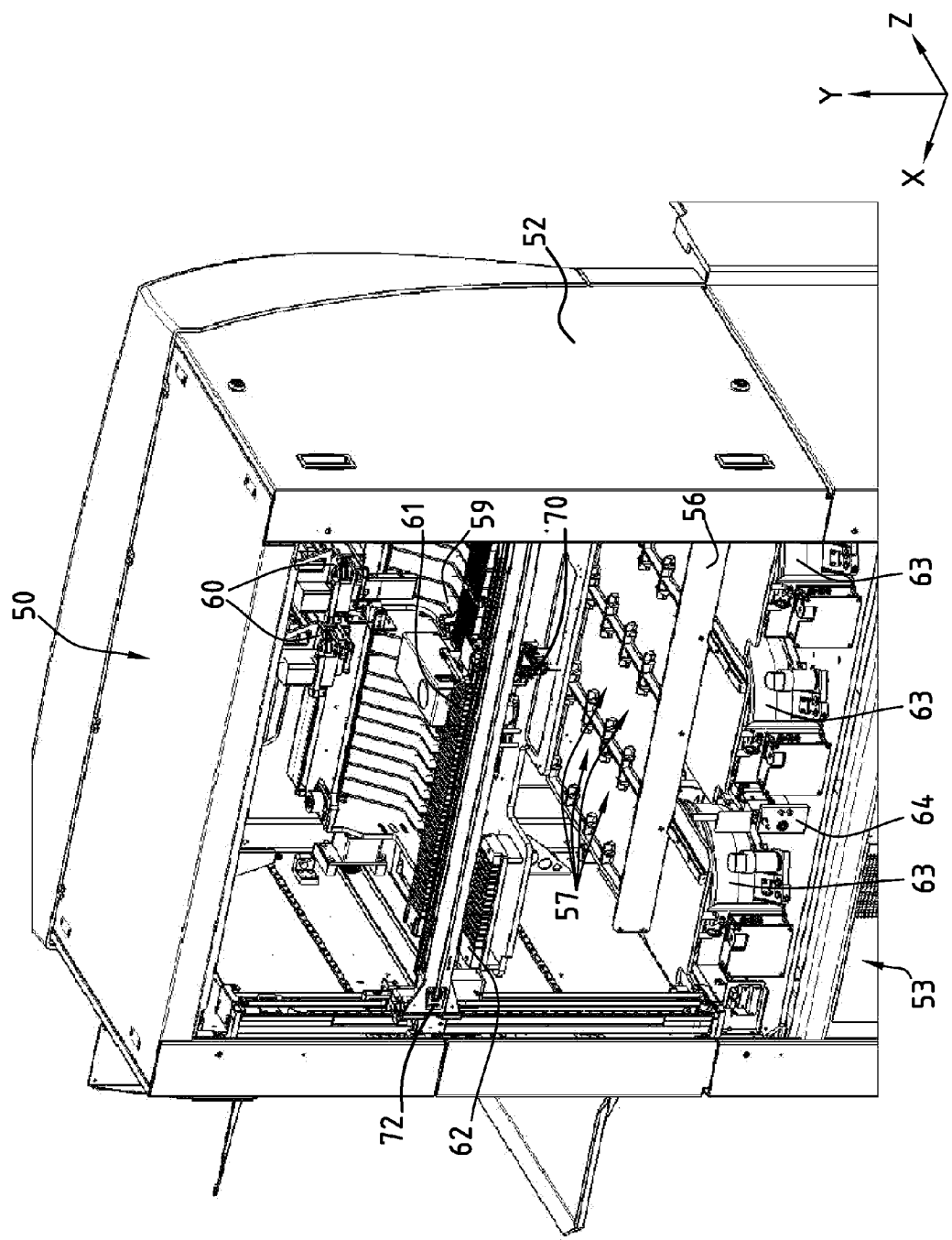
FIG. 3 is a perspective view of a machine comprising a clamp intended to grip both gel cards and microplates.

In reference to FIG. 3, the general reference 50 designates a machine intended for the treatment and analysis of biological samples, whether they are received in gel cards or microplates.

In the following description, the positioning and orientation of the elements of the machine 50 will be done in reference to an orthogonal reference with axes X, Y, Z, attached to the machine 50. In the normal usage position of the machine 50, the Y axis is intended to be vertical. The Y axis thus defines a vertical direction Y. Moreover, in the normal usage position of the machine 50, the X and Z axes are intended to extend horizontally. The X axis defines a longitudinal direction X, and the Z axis defines a transverse direction Z.

The machine 50 comprises an enclosure 52 in cabinet form with a length along the longitudinal direction X and a width along the transverse direction Z. The enclosure 52 comprises an open longitudinal rear face 53 and a pivoting flap for closing the open face 53.

The machine 50 comprises, in the enclosure 52, a drawer 56 for storing gel cards and microplates. The drawer 56 is translationally mounted along the transverse axis Z such that the drawer 56 can be opened towards the front of the machine 50. The drawer 56 comprises a plurality of locations 57, each location 57 being designed to receive either a microplate, or a basket of gel cards, in which the gel cards are aligned, with their main walls substantially parallel to each other.

The machine 50 comprises, in the enclosure 52, transverse corridors 59 for loading test tubes or biological sample bottles, a longitudinal ramp 61 for receiving gel cards or microplates, and pipetting robots 62 for the gel cards or microplates received on the ramp 61.

The ramp 61 comprises transverse slots, each designed to receive the main wall of a gel card, or one of the transverse walls 38C, 38D of a microplate.

The machine 50 comprises, in the enclosure 52, an incubator 62 having the same shape as the ramp 61 and also comprising a heating device.

The machine comprises, in the enclosure 52, gel card centrifuges 63 and an analysis device 64 for biological samples contained in a gel card.

The machine 50 is also suitable for receiving a device for analyzing biological samples contained in a microplate.

The machine 50 also comprises a clamp 70 intended to grip one of the holders arranged in the machine 50, whether gel card or microplate, each time.

The machine 50 comprises a hinged transport arm 72 of the clamp 70. The transport arm 72 is hinged along all three dimensions of the space, so as to be able to move the clamp 70 between the storage drawer 56 and the treatment stations 61, 62, 63 and 64. The hinged arm 72 makes the clamp 70 always keep the same orientation.

Figure 4:
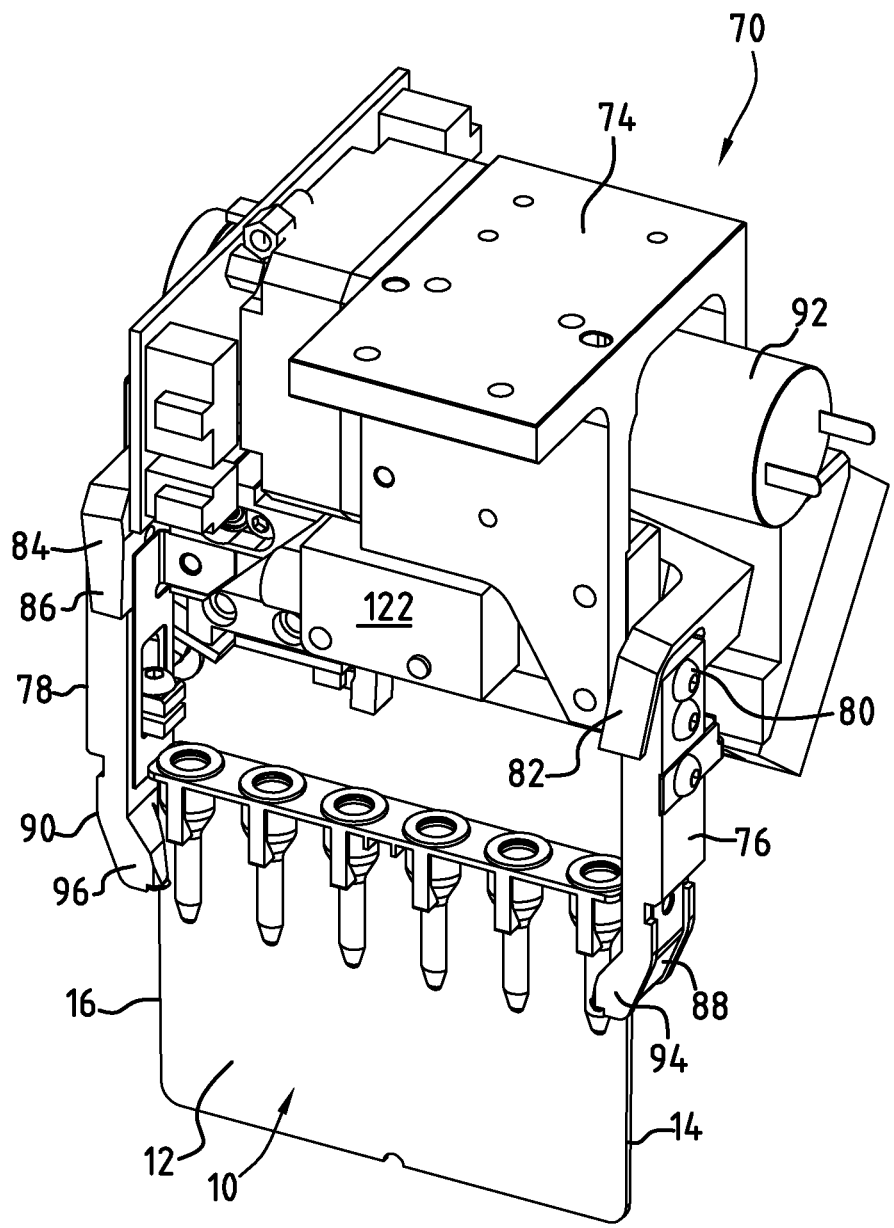
FIGS. 4 and 5 are perspective views of the clamp gripping a gel card.
Figure 5:
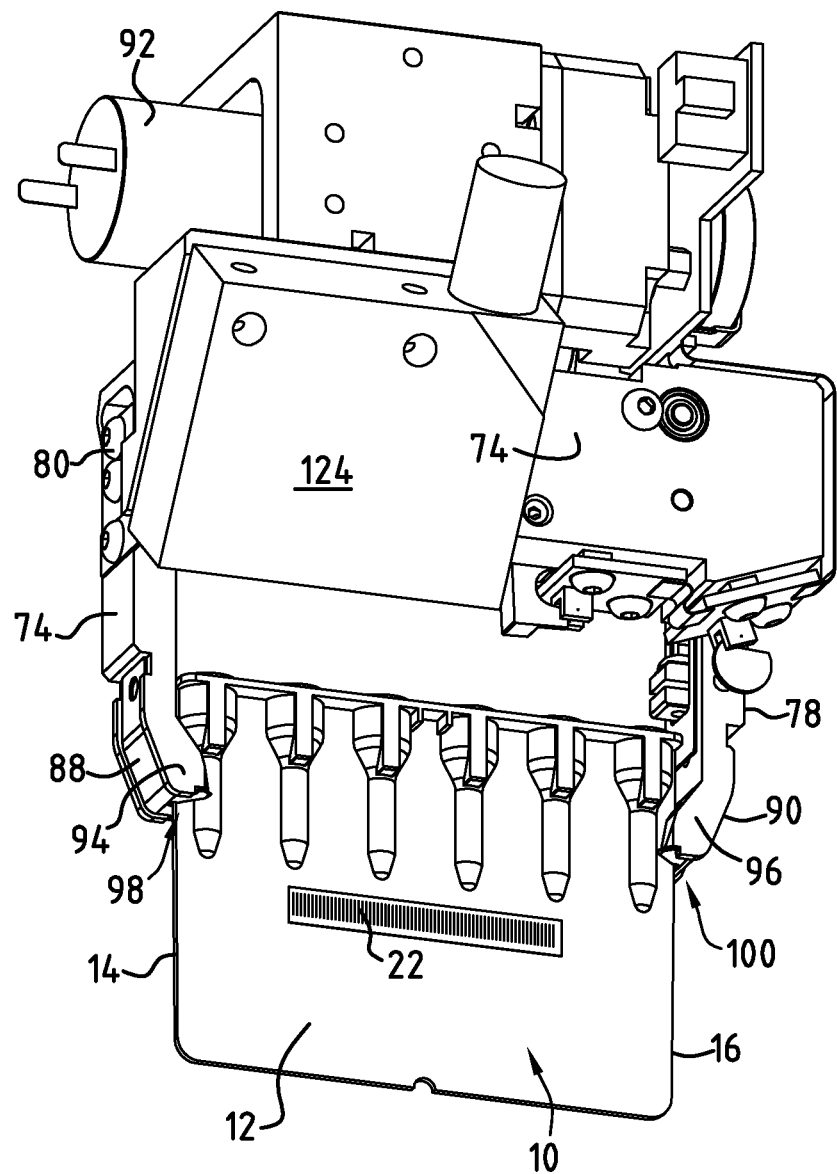
Figure 6:
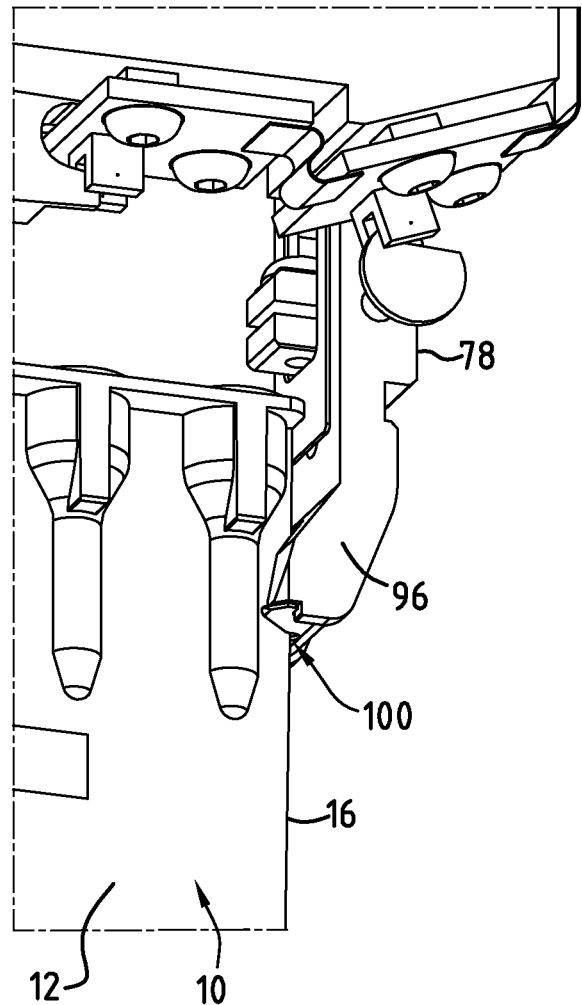
FIG. 6 is a perspective view of an arm of the clamp.

In reference to FIGS. 4 to 6, the clamp 70 is shown gripping a gel card 10.

The clamp 70 comprises an upper base 74 intended to be fixed to the hinged arm 72, and first and second arms 76, 78 extending downwards, from the base 74.

The first arm 76 is provided with a first upper end 80 connected to the base 74 by a first pivot link 82 in the longitudinal direction X, and the second arm 78 is provided with a second upper end 84 connected to the base 74 by a second pivot link 86 along longitudinal direction X. The first and second arms 76, 78 are thus configured to pivot along the longitudinal direction X in relation to the base 74, in the vertical plane YZ.

The first arm 76 is also provided with a first lower end 88 for gripping the gel card 10, and the second arm 78 is also provided with a second lower end 90 for gripping the gel card 10. The first and second lower ends 88, 90 are intended to grip the gel card 10 by squeezing it.

The base 74 comprises a rotary electric motor 92 for driving, via a "small mechanics" type movement transmission device, the first and second arms 76, 78 of the clamp 70, so as to make the first and second arms 76, 78 go between a first position, illustrated in FIGS. 4 and 5, of gripping the gel card 70, and a position of releasing the gel card 10. When the first and second arms 76, 78 are in the releasing position, the first and second gripping ends 88, 90 are spaced away from each other along the transverse direction Z. When the first and second arms are in the first gripping position, the first and second gripping ends 88, 90 are brought closer to each other along the transverse direction Z.

The first gripping end 88 comprises a first protruding portion 94, oriented towards the second arm 78, and the second gripping end 90 comprises a second protruding portion 96, oriented towards the first arm 76. When the arms 76, 78 are in the gripping position, the first and second protruding portions 94, 96 protrude vertically, in relation to the direction Y, relative to their respective arms 76, 78.

The first arm 76 comprises a first groove 98 for receiving the vertical wall 12 of the gel card 10, formed in the first protruding portion 94. Similarly, the second arm 78 comprises a second groove 100 for receiving the vertical wall 12 of the gel card 10, formed in the second protruding portion 96. The first and second grooves 98, 100 extend in the vertical plane YZ, i.e. the vertical plane YZ passes in each of the first and second grooves 98, 100. Both ends of the first and second grooves 98, 100 are open.

Figure 7:
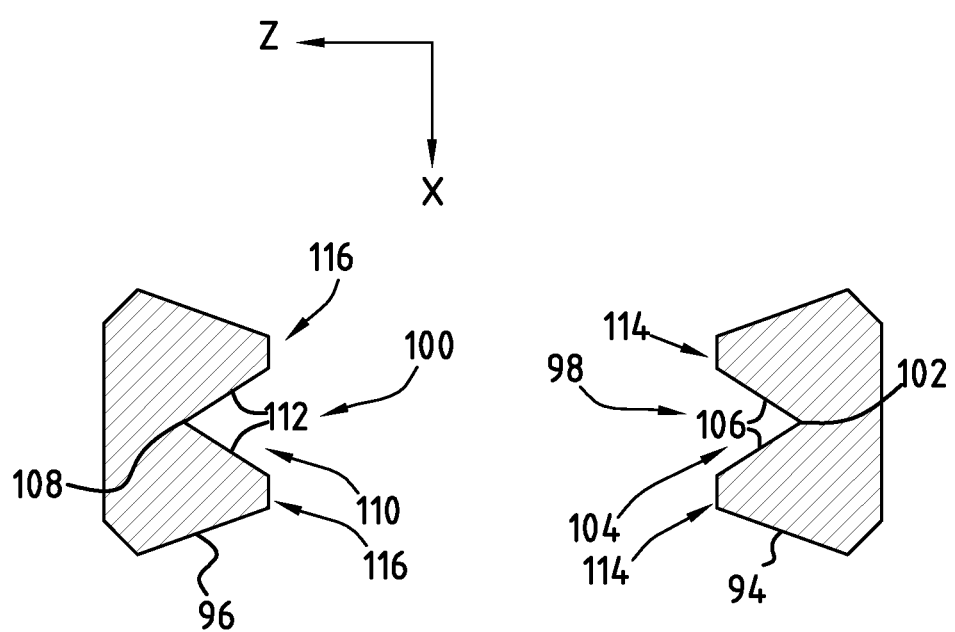
FIG. 7 is a cross-sectional view of the arms of the clamp.

In reference to FIG. 7, the first groove 98 is provided with a bottom 102, an opening 104 opposite the bottom 102, and side walls 106 connecting the bottom 102 to the opening 104. The first groove 98 has a transverse profile, i.e. in the horizontal plane XZ when the arms 76, 78 are in the first gripping position, V-shaped along a first groove direction, perpendicular to the plane of FIG. 7. The side walls 106 thus meet the bottom 102, and move away from each other as they move away from the bottom 102 towards the opening 104. When the first and second arms 76, 78 are in the gripping position, the first groove direction is vertical.

The second groove 100 is identical to the first groove 98 and thus comprises a bottom 108, an opening 110, side walls 112 and a second groove direction, all arranged in the same way as for the first groove 98.

The separation along the transverse axis Z between the first and second grooves 98, 100 is greater in the position of release than in the gripping position of the gel card. More specifically, the side walls 106 and 112 are separated along the transverse direction Z, in the position of release, by a distance greater than the distance d1, and, in the first gripping position, by a distance equal to the distance d1.

Figure 8:
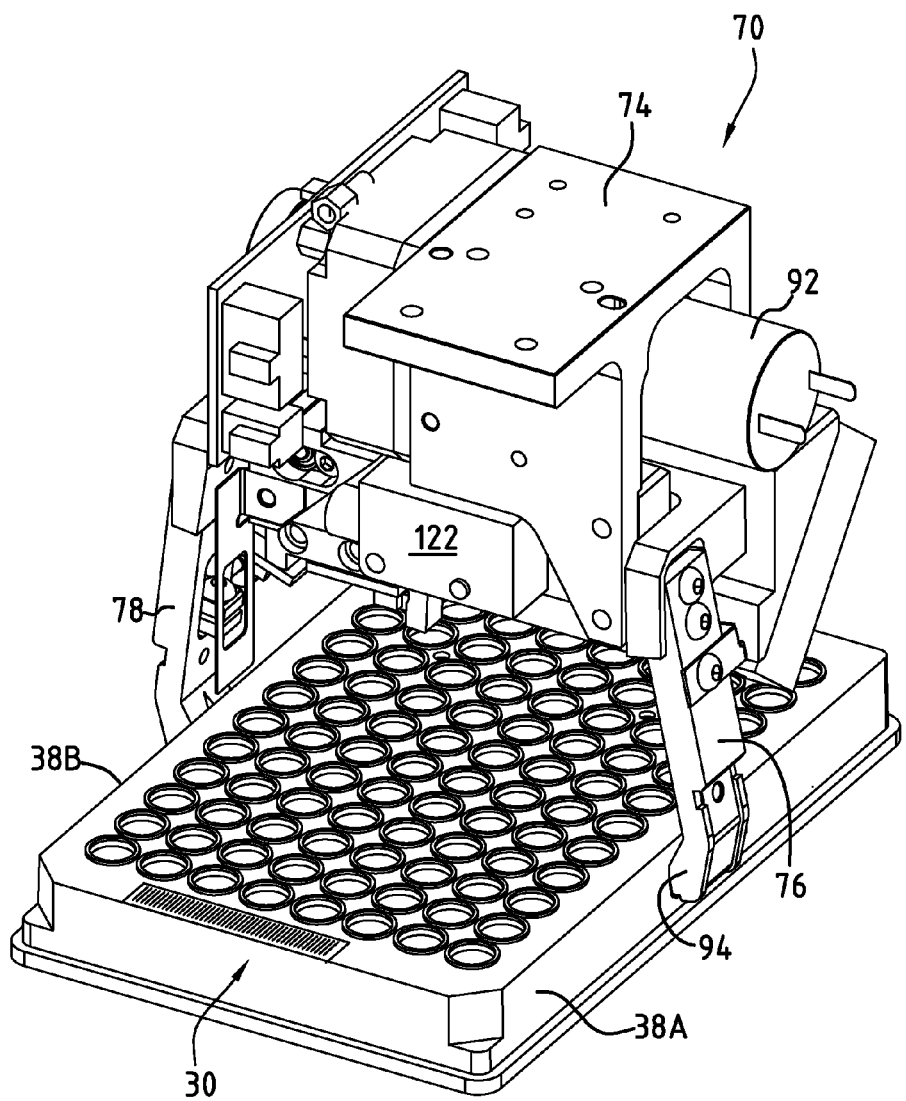
FIGS. 8 and 9 are perspective views of the clamp gripping a microplate.
Figure 9:
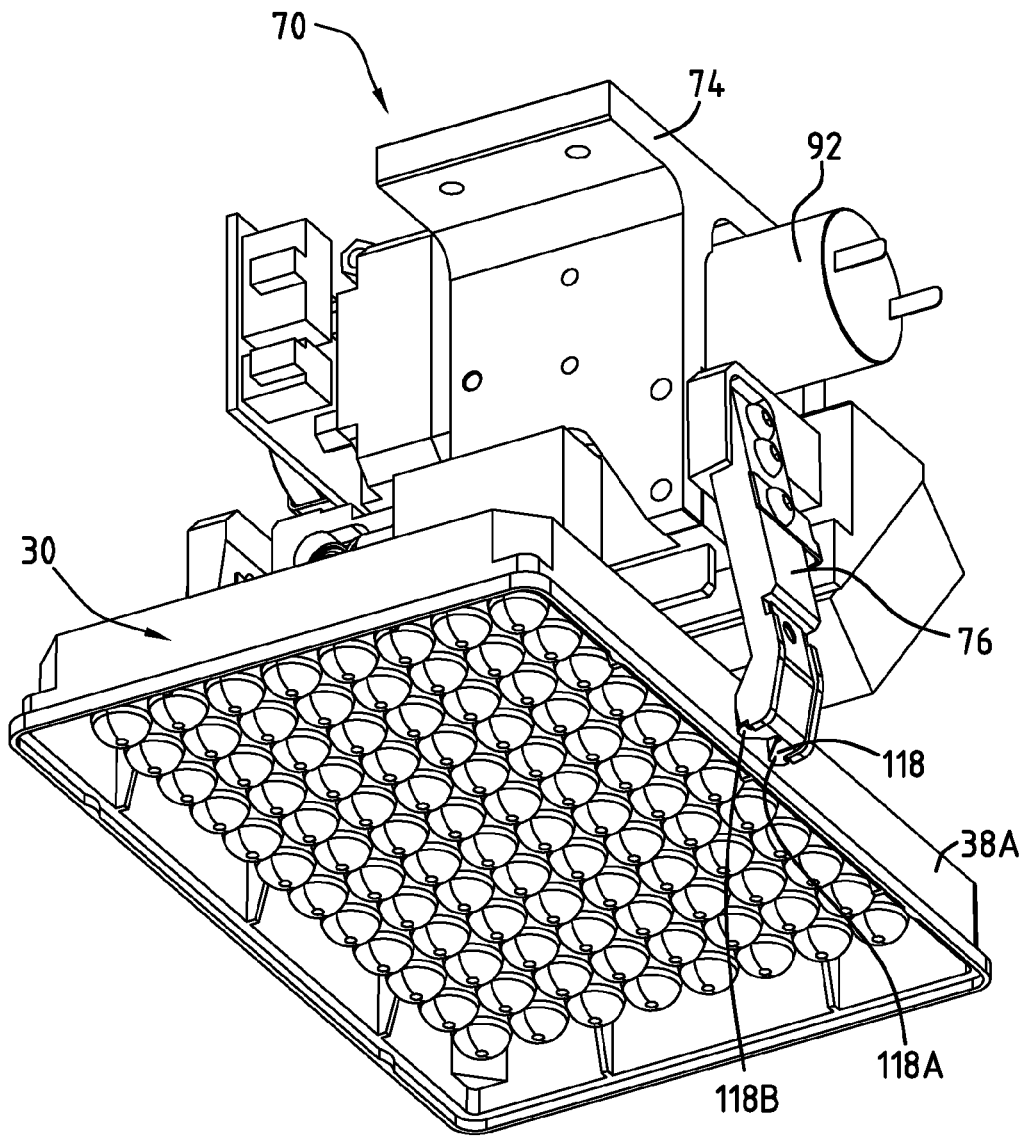
Figure 10:
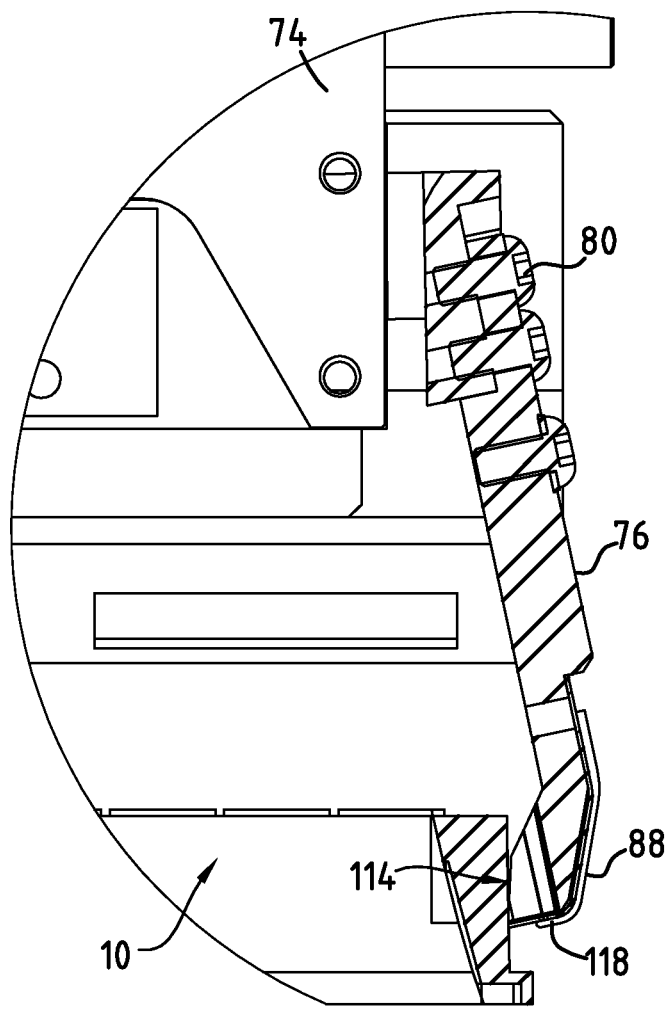
FIG. 10 is a cross-sectional view of an arm of the clamp gripping the microplate.

In reference to FIGS. 8 to 10, the clamp 70 is shown gripping a microplate 30.

To that end, the first protruding portion 94 comprises a first forward contact face 114 with the first lateral wall 38A of the microplate 30, and the second protruding portion 96 comprises a second forward contact face 116 with the second lateral wall 38B of the microplate 30.

The motor 92 is also configured to move the first and second arms 76, 78 between the position of release and a second gripping position of the microplate 30. Since the distance d2 is greater than the distance d1, the second gripping position is situated between the position of release and the first gripping position.

When the first and second arms 76, 78 are in the second gripping position, the first and second forward faces 114, 116 are brought closer, relative to the position of release, to each other along the transverse direction Z and are opposite each other, so as to be able to contact, respectively, the first lateral wall 38A and the second lateral wall 38B of the microplate 30, in order to grip the microplate 30 by squeezing of the first and second lateral walls 38A, 38B along the transverse direction Z.

More precisely, the first and second contact faces 114, 116 are separated along the transverse direction Z, in the position of release, by a distance greater than d2, and, in the gripping position of the microplate, by a distance substantially equal to d2.

Moreover, the first and second contact faces 114, 116 are each inclined relative to their respective arms 76, 78 such that, in the gripping position, they are substantially parallel to each other.

The first contact face 114 is separated in two by the first groove 98, and the second contact face 116 is separated in two by the second groove 100.

The first arm 76 also comprises a first blade 118 overhanging relative to the first contact face 114, the first overhanging blade 118 comprising two ends 118A, 118B overhanging, each arranged on a respective side of the first groove 98. Similarly, the second arm 78 also comprises a second overhanging blade 120 relative to the second contact face 116, the second overhanging blade comprising two overhanging ends 120A, 120B, each arranged on a respective side of the second groove 100.

The first overhanging blade 118, and in particular each end 118A, 118B, is intended to be folded in contact with the first lateral wall 38A, in order to reduce the sliding between the first contact face 114 and the first lateral wall 38A. Similarly, the second overhanging blade 120, and in particular each end 120A, 120B, is intended to be folded in contact with the second lateral wall 38B, in order to reduce the sliding between the second contact face 116 and the second lateral wall 38B. Preferably, each end 118A, 118B, 120A, 120B has an upwardly curved shape, towards the base 74 of the clamp 70, such that each end 118A, 118B, 120A, 120B is folded upwards in contact with the microplate 30. Thus, during transport, the weight of the microplate 30 tends to unfold the ends downwardly, which pushes said ends that much more against the walls 38A, 38B, and thereby increases the friction with said walls, thereby reducing the risk of sliding. The first and second overhanging blades thus reduce the risk of the microplate 30 escaping the clamp 70.

FIG. 10 illustrates the contact between the first arm 76 and the first lateral face 38A of the microplate 30.

In reference to FIGS. 4 and 8, the clamp 70 also comprises a device 122 for detecting the presence of a gel card or a microplate, gripped by the clamp 70. It is for example an optical reflection sensor.

Figure 11:
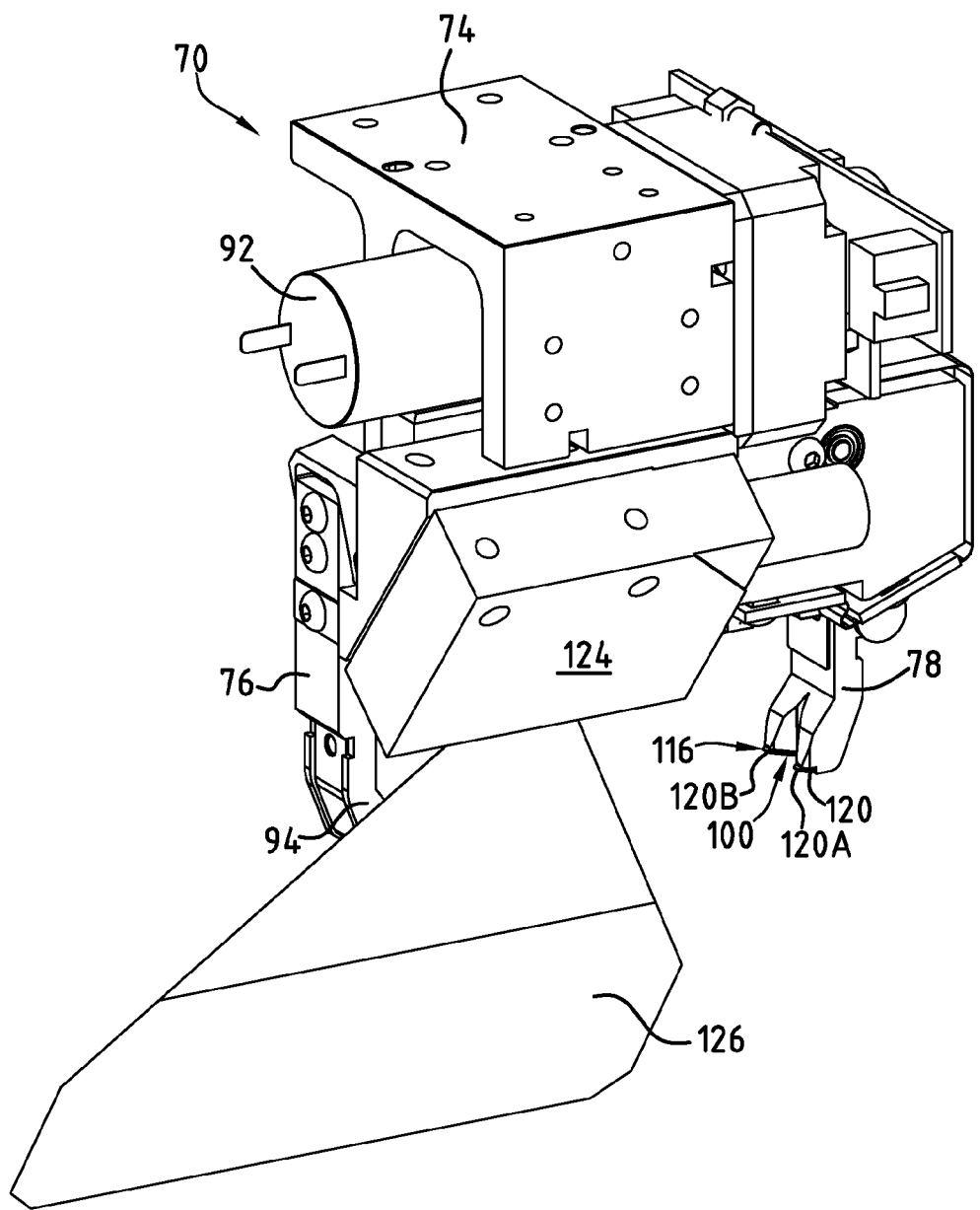
FIG. 11 is a perspective view of the clamp, illustrating the operation of a barcode reader of the clamp.

In reference to FIG. 11, the clamp 70 also comprises a barcode reader 124 having a reader beam 126 intended to enable reading of the barcode of the gel card 10 and that of the microplate 30.

We will now describe an example of the operation of the machine 50.

An operator opens the drawer 56, places baskets containing empty gel cards and/or empty microplates in the location 57, then closes the drawer 56 again.

The operator loads the test tubes and/or bottles containing the biological samples, for from example patients, in the transverse corridors 59.

The arm 72 moves the clamp 70 to read the barcodes of the stored empty gel cards.

The clamp 70 grips an empty gel card, selected for example by its barcode. Owing to the advantageous shape of the grooves 98, 100, the gel card is gripped even if its placement in the basket is approximate.

The arm 72 moves the clamp 70 to the ramp 61, where the clamp 70 releases the gel card.

One of the robots 60 then transfers the biological samples into the receptacles 18 of the gel card placed on the ramp 61.

In the same way as before, the gel card is moved by the clamp 70 successively in the incubator 62, then in one of the centrifuges 63, then in the analysis device 64.

Similarly, the arm 72 moves the clamp 70 onto the drawer 56, where the clamp 70 grips an empty microplate. The arm 72 moves the clamp 70 onto the ramp 61, where the clamp 70 releases the microplate.

One of the robots 60 then transfers biological samples into the receptacles of the microplate placed on the ramp 61.

The arm 72 and the clamp 70 then transfer the microplate containing the biological samples either to the drawer 56, where the operator can recover it to perform additional treatments outside the machine 50, or to the station for analyzing microplate biological samples, when the latter is provided in the machine 50.

What is claimed is:

1. A machine for gripping different biological sample holders comprising:
   a storage location storing at least a first biological sample holder and a second sample holder;
   the first biological sample holder comprising a wall with two opposite lateral edges extending longitudinally in a vertical direction and biological sample receptacles carried by the wall and emerging through a horizontal rim connecting the two lateral edges, the wall extending vertically with the lateral edges and the receptacles opening upwardly;
   the second biological sample holder comprising first and second opposite parallel lateral walls extending longitudinally in the horizontal direction, an upper horizontal wall connecting the first and second lateral walls and biological sample receptacles being carried by the upper wall, the first and second lateral walls extending in the vertical direction, with the receptacles emerging upwardly,
   a hinged arm to which a clamp for gripping the first biological sample holder is fixed, the clamp comprising a first arm and a second arm moveable relative to each other along a gripping direction between a first position of gripping the first biological sample holder and a first position of releasing the biological sample holder, wherein the first arm of the clamp comprises a first contact face that is separated into two flat surfaces by a first groove formed therebetween, the second arm of the clamp comprises a second contact face that is separated into two flat surfaces by a second groove formed therebetween, and;
   a controller in communication with the hinged arm and configured to operate according to the following steps:
   gripping the first biological sample holder using the clamp along a gripping direction,
   moving the first and second arms of the clamp such that the first and second grooves extend longitudinally in the vertical direction, from a position of release, in which the first and second grooves are spaced away from each other along the gripping direction up to a first gripping position, the first and second grooves being brought closer to each other along the gripping direction, extending opposite each other, and receiving the lateral edges of the first biological sample holder, in order to grip the first biological sample holder by squeezing the lateral edges along the gripping direction, gripping, in place of the first biological sample holder the second biological sample holder, gripping of the second biological sample holder including through the movement of the first and second arms from a second position of release, wherein each of flat surfaces of the first contact face and the flat surfaces of the second contact face are spaced away from each other along the gripping direction up to a second gripping position, in which the first and second contact faces are brought closer to each other along the gripping direction, are opposite each other, and contact, respectively, the first lateral wall and the second lateral wall of the second biological sample holder, so as to grip the second biological sample holder by squeezing the first and second lateral walls along the gripping direction.

2. The machine according to claim 1, wherein the second biological sample holder is a microplate.

3. The machine according to claim 1, wherein the first and second contact faces are each inclined relative to their respective arms such that, in the second gripping position, they are substantially parallel to each other.

4. The machine according to claim 1, wherein the first arm has a first protruding portion comprising the first contact face and the second arm has a second protruding portion comprising the second contact face such that, when the first arm and the second arm are in the first gripping position, the first protruding portion and second protruding portion protrude in relation to their respective arms along the gripping direction, the first groove is formed in the first protruding portion and the second groove is formed in the second protruding portion.

5. The machine according to claim 4, wherein the first protruding portion includes two first protruding sections extending longitudinally in the vertical direction that are on opposite sides of the first groove, the second protruding portion including two second protruding sections extending longitudinally in the vertical direction that are on opposite sides of the second groove.

6. The machine according to claim 5, wherein the first groove is defined by two first side walls each angled with respect to the first contact face, the second groove being defined by two second side walls each angled with respect to the second contact face.

7. The machine according to claim 1, wherein the first contact face and the second contact face are able to not contact the first biological sample holder when the first arm and the second arm are in the first gripping position, the first and second groves receiving the lateral edges of the first biological sample holder, and the two first side walls and the two second side walls are able to not contact the second biological sample holder when the first and second arms are in the second gripping position, the first contact face contacting the first parallel lateral wall of the second biological sample holder and the second contact face contacting the second parallel lateral wall of the second biological sample holder.

8. The machine according to claim 1, wherein the first arm comprises a first device for reducing sliding with the first lateral wall and the second arm comprises a second device for reducing sliding with the second lateral wall.

9. The machine according to claim 8, wherein the first device for reducing sliding comprises a first blade overhanging relative to the first contact face, the first overhanging blade to be folded in contact with the first lateral wall and the second device for reducing sliding comprises a second blade overhanging relative to the second contact face, the second overhanging blade to be folded in contact with the second lateral wall.

10. The machine according to claim 1, wherein the first biological sample holder is a gel card.

11. The machine according to claim 1, wherein the biological sample receptacles emerge through a rim connecting the two lateral edges.

* * * * *